US012797255B2

(12) United States Patent
Stoll

(10) Patent No.: US 12,797,255 B2
(45) Date of Patent: Nov. 17, 2026

(54) HYDROCOLLOID HEEL PATCH AND METHODS

(71) Applicant: Catherine Ross Stoll, Palo Alto, CA (US)

(72) Inventor: Catherine Ross Stoll, Palo Alto, CA (US)

( * ) Notice: Subject to any disclaimer, the term of this patent is extended or adjusted under 35 U.S.C. 154(b) by 36 days.

(21) Appl. No.: 18/663,970

(22) Filed: May 14, 2024

(65) Prior Publication Data

US 2024/0382348 A1 Nov. 21, 2024

Related U.S. Application Data

(60) Provisional application No. 63/467,313, filed on May 18, 2023.

(51) Int. Cl.
*A61F 13/00* (2024.01)
*A61F 13/0246* (2024.01)
(Continued)

(52) U.S. Cl.
CPC ........ *A61F 13/064* (2013.01); *A61F 13/0253* (2013.01); *A61K 8/31* (2013.01)

(58) Field of Classification Search
CPC .......... A61K 8/0208; A61K 8/31; A61K 8/42; A61K 8/92; A61K 8/8117; A61K 8/731; A61K 8/368; A61Q 19/007; A61Q 19/00; A61F 13/00063; A61F 13/069; A61F 13/067; A61F 13/064
See application file for complete search history.

(56) References Cited

U.S. PATENT DOCUMENTS 5,713,842 A * 2/1998 Kay ...................... A61F 13/023 602/41
6,384,293 B1 * 5/2002 Marcussen .......... A61F 13/0259 602/41
(Continued)

FOREIGN PATENT DOCUMENTS

JP 3137853 U * 12/2007 ........... A61K 8/0208

OTHER PUBLICATIONS

Hydrocolloid patches for Dry Cracked Heels https://www.amazon.com/Healz-Hydrocolloid-Patches-Cracked-Heels/dp/B0C9787XG2?th=1 (Year: 2023).*
(Continued)

*Primary Examiner* — Kim M Lewis
(74) *Attorney, Agent, or Firm* — David Meibos; Maywood IP Law

(57) ABSTRACT

A method for treating a fissure of a heel, wherein the fissure extends from a side and/or back portion of the heel to a bottom portion of the heel, may include positioning a patch proximate the fissure. The patch may include an exterior-facing side formed of a flexible material, a skin-facing side comprising an adhesive material configured to adhere to the skin of the heel, a central portion having a first thickness, and an outer edge having a second thickness equal to the first thickness; wherein one of the exterior-facing side and the skin-facing side may include a hydrocolloid material. The method may further include applying the patch to the fissure such that the adhesive material retains the patch on the side and/or back portion of the heel and the bottom portion of the heel.

19 Claims, 7 Drawing Sheets

(51) Int. Cl.
*A61F 13/06* (2006.01)
*A61K 8/31* (2006.01)

(56) References Cited

U.S. PATENT DOCUMENTS 6,822,132 B2 * 11/2004 Ahrens .................. A61F 13/023 602/41
7,049,478 B1 * 5/2006 Smith .................... A61F 13/067 128/892
7,091,394 B2 * 8/2006 Kolte .................. A61F 13/0203 602/42
7,141,713 B2 * 11/2006 Agrama ................ A61F 13/064 602/41
8,080,703 B2 * 12/2011 Marcussen ............ A61F 13/061 424/443
12,011,343 B2 * 6/2024 Devlin .................. A61F 13/067
2005/0033211 A1 * 2/2005 Scheinberg ........... A61F 13/069 602/43
2005/0266059 A1 12/2005 Poss
2009/0065014 A1 * 3/2009 Nagata .................. A61F 13/067 132/73
2020/0093647 A1 * 3/2020 McClendon ...... A61F 13/00063
2020/0121515 A1 * 4/2020 Sakotic ................ A61Q 19/007
2020/0306093 A1 * 10/2020 Rivest ..................... A61F 13/00
2022/0186090 A1 6/2022 Sieverding
2022/0401268 A1 * 12/2022 Devlin .................... A61F 13/06

OTHER PUBLICATIONS

Band Aid, Band-Aid Brand Adhesive Bandages Hydro Seal Wound Care Bandages, Hydrocolloid Gel Heel Bandages Support Better Healing for Blisters, Cuts & Scrapes, Long Lasting Waterproof Bandages, sold on Amazon—accessed Sep. 21, 2024.

* cited by examiner

HYDROCOLLOID HEEL PATCH AND METHODS

CROSS-REFERENCE TO RELATED APPLICATIONS

The present application claims the benefit of U.S. Provisional Patent Application No. 63/467,313 filed on May 18, 2023, entitled HYDROCOLLOID PATCH TO HEAL DRY CRACKED HEELS, which is incorporated by reference as though set forth herein in its entirety.

TECHNICAL FIELD

The present disclosure relates generally to devices and methods for treating dry skin, and more particularly, to devices and methods for treating dry cracked skin, or fissures, on a heel of a foot.

BACKGROUND

Dry cracked heels, or heel fissures, are a common problem affecting many individuals. Current treatments include moisturizing creams and lotions, which often provide temporary relief but fail to address the underlying causes and provide long-lasting healing. Therefore, there is a need for an improved solution that promotes effective healing of dry cracked heels or heel fissures.

SUMMARY

The various systems and methods of the present disclosure have been developed in response to the present state of the art, and in particular, in response to the problems and needs in the art that have not yet been fully solved by currently available devices and methods for interspinous-interlaminar stabilization systems.

In some embodiments, a method for treating a fissure of a heel, wherein the fissure extends from a side and/or back portion of the heel to a bottom portion of the heel, may include positioning a patch proximate the fissure. The patch may include an exterior-facing side formed of a flexible material, a skin-facing side comprising an adhesive material configured to adhere to the skin of the heel, a central portion having a first thickness, and an outer edge having a second thickness equal to the first thickness; wherein one of the exterior-facing side and the skin-facing side may include a hydrocolloid material. The method may further include applying the patch to the fissure such that the adhesive material retains the patch on the side and/or back portion of the heel and the bottom portion of the heel.

In the method of any preceding paragraph, both the exterior-facing side and the skin-facing side may include the hydrocolloid material.

In the method of any preceding paragraph, the method may also include opening a sterile package containing the patch and removing the patch from the sterile package.

In the method of any preceding paragraph, the patch may further include an ellipse shape having a uniform thickness.

In the method of any preceding paragraph, the ellipse shape may have an aspect ratio of 2:1.

In the method of any preceding paragraph, the ellipse shape may include a major axis less than or equal to 60 mm and a minor axis less than or equal to 30 mm.

In the method of any preceding paragraph, the adhesive material may be configured so that 1) the patch remains in place after application and 2) the patch is removeable from the heel without causing damage to the skin of the heel or the fissure.

In some embodiments, a method for treating a fissure of a heel, wherein the fissure extends from a side and/or back portion of the heel to a bottom portion of the heel, may include positioning a patch proximate the fissure. The patch may include an exterior-facing side formed of a flexible material, a skin-facing side comprising an adhesive material configured to adhere to the skin of the heel; wherein one of the exterior-facing side and the skin-facing side includes a hydrocolloid material. The method may further include applying the patch to the fissure such that the adhesive material retains the patch on the side and/or back portion of the heel and the bottom portion of the heel; wherein the patch may further include an ellipse shape comprising a uniform thickness and the ellipse shape includes a major axis less than or equal to 60 mm and a minor axis less than or equal to 30 mm.

In the method of any preceding paragraph, both the exterior-facing side and the skin-facing side may include the hydrocolloid material.

In the method of any preceding paragraph, the ellipse shape may have an aspect ratio of 2:1.

In the method of any preceding paragraph, the adhesive material may be configured so that 1) the patch remains in place after application and 2) the patch is removeable from the heel without causing damage to the skin of the heel or the fissure.

In the method of any preceding paragraph, the method may also include opening a sterile package containing the patch and removing the patch from the sterile package.

In the method of any preceding paragraph, the patch may be flat within the sterile package.

In some embodiments, a method for treating a fissure of a heel, wherein the fissure extends from a side and/or back portion of the heel to a bottom portion of the heel, may include opening a sterile package containing a patch, wherein the patch is flat within the sterile package. The patch may further include an exterior-facing side formed of a flexible material and a skin-facing side including an adhesive material configured to adhere to the skin of the heel, wherein one of the exterior-facing side and the skin-facing side includes a hydrocolloid material. The method may further include, removing the patch from the sterile package, positioning the patch proximate the fissure, and applying the patch to the fissure such that the adhesive material retains the patch on the side and/or back portion of the heel and the bottom portion of the heel.

In the method of any preceding paragraph, both the exterior-facing side and the skin-facing side may include the hydrocolloid material.

In the method of any preceding paragraph, the ellipse shape may have an aspect ratio of 2:1.

In the method of any preceding paragraph, the ellipse shape may have a major axis less than or equal to 60 mm and a minor axis less than or equal to 30 mm.

In the method of any preceding paragraph, the adhesive material may be configured so that 1) the patch remains in place after application and 2) the patch is removeable from the heel without causing damage to the skin of the heel or the fissure.

In the method of any preceding paragraph, the patch may further include a central portion having a first thickness and an outer edge having a second thickness equal to the first thickness.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the disclosure will be described with additional specificity and detail through use of the accompanying drawings in which:

DETAILED DESCRIPTION

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, system, and method, as represented in FIGS. 1A through 9, is not intended to limit the scope of the claims, but is merely representative of exemplary embodiments of the disclosure.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The device and method of use in accordance with the present application may overcome one or more of the above-discussed problems commonly associated with dry cracked heels. These and other unique features of the device and method of use are discussed below and illustrated in the accompanying drawings.

Figure 1A:
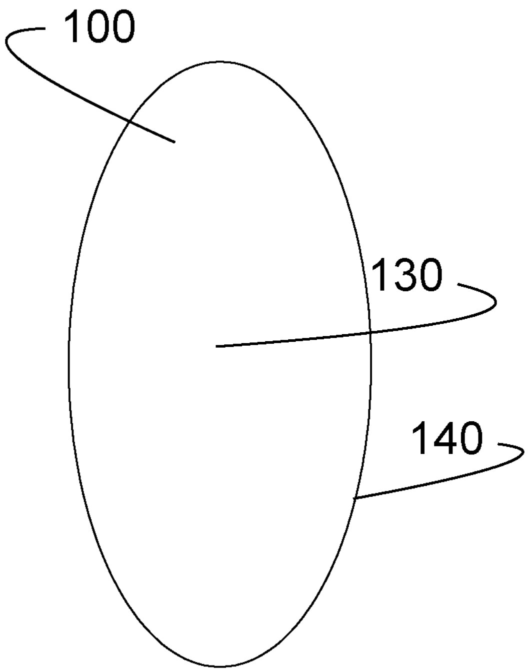
FIG. 1A is a front view of a hydrocolloid heel patch according to one embodiment of the present disclosure.

FIG. 1A is a front view of a hydrocolloid heel patch 100 according to one embodiment of the present disclosure. The patch 100 may be constructed from a soft and flexible material that adheres securely to the heel while promoting healing. The patch may be configured to treat dry cracked heels and/or heel fissures. The patch 100 may treat a specific area of dry cracked heels and/or heel fissures, providing localized treatment for maximum effectiveness.

The patch 100 may be configured to be easily applied to a heel and may be worn discreetly under socks and/or shoes, allowing users to continue their daily activities while benefiting from the healing process. The patch 100 may help the skin retain its own moisture.

The patch 100 may be configured to be hypoallergenic, sterile, and/or suitable for individuals with sensitive skin. The patch 100 may be pre-packaged in a manner designed to preserve sterility, for example, in an airtight seal or another antimicrobial barrier. The patch 100 may have a skin-facing side 120 covered by an adhesive material such that the patches are able to adhere to the skin of a heel 50. The adhesive may be configured such that adhesive material retains the patch on a heel. Additionally, the adhesive may be configured so that the patch may be removed from the heel 50 without causing damage to the skin or a fissure of the heel 50.

Figure 1B:
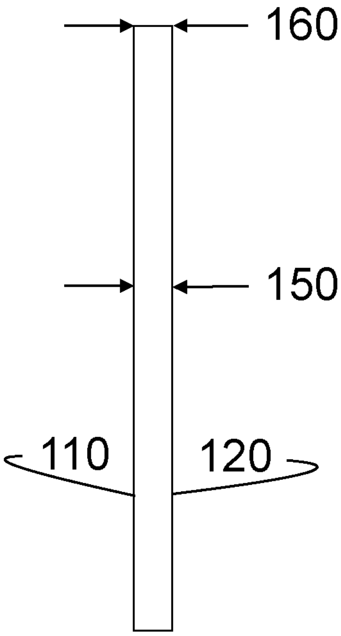
FIG. 1B is a side view of the hydrocolloid heel patch of FIG. 1A.

FIG. 1B is a side view of the hydrocolloid heel patch 100. The patch 100 may include a central portion 130 and an outer edge 140. The central portion may include a first thickness 150 and the outer edge may include a second thickness 160. The patch 100 may be configured so that the first thickness 150 is generally equal to the second thickness 160.

Figure 2:
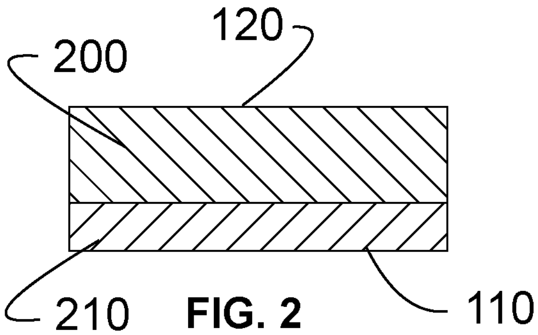
FIG. 2 is a partial cross-section view of the hydrocolloid heel patch of FIG. 1A.

FIG. 2 is a partial cross-section view of the hydrocolloid heel patch 100. The patch 100 may include two or more layers including an adhesive material 200 and a flexible material 210. The patch 100 may be fabricated by laminating the two or more layers into a sheet and die cutting the patch 100 from the laminated sheet. The die cutting process may ensure that the first thickness 150 is generally equal to the second thickness 160 and that the ellipse has a uniform thickness.

The patch 100 may further include an exterior-facing side 110 and a skin-facing side 120. The adhesive material 200 may be proximate the skin-facing side 120. The flexible material 210 may be proximate the exterior-facing side 110

The skin-facing side 120 may be configured to adhere directly to the skin of a heel. The skin-facing side 120 may include adhesive properties inherent in the adhesive material 200. For example, the adhesive material 200 may include a pressure sensitive adhesive, for example: rubber-based, acrylic-based and/or silicone-based pressure sensitive adhesive. Additionally, or alternatively, the skin-facing side 120 may include a second adhesive that is different than the adhesive material 200. The adhesive material may be latex-free.

The adhesive material 200 may be configured so that the patch 100 may remain in place after application of the patch 100 proximate the fissure. Additionally, the adhesive material 200 may be configured so that the patch 100 may be removed from the heel without causing damage to the skin of the heel or a fissure. Additionally, or alternatively, the adhesive material 200 may be configured such that, upon removal of the patch 100 from the heel, no adhesive residue remains on the skin of the heel or the fissure. The adhesive material 200 may include a medical grade hot melt adhesive.

The adhesive material 200 may include a hydrocolloid material comprising gelatin, pectin, carboxymethyl cellulose and/or other hygroscopic particles. The hydrocolloid material may be selected to absorb water and/or moisture from the skin that is in contact with the patch 100 and retain the moisture within the patch 100 forming a hydrocolloid gel. The hydrocolloid gel may create conditions under the patch 100 which may beneficially result in an environment conducive to the formation of keratinocytes and/or other types of skin cells. Additionally, the moist environment may help to expedite the removal of dead tissue.

The flexible material 210 may include a film and/or foam. The flexible material 210 may be configured to form a moisture barrier to maintain the moist environment between the adhesive material 200 and the skin. Additionally, or alternatively, the flexible material 210 may be configured to provide structural support to the adhesive material 200 to maintain the shape of the patch 100. Additionally, or alternatively, the flexible material 210 may be configured to prevent shearing and/or decomposition of the adhesive material 200.

Additionally, or alternatively, the flexible material 210 may also include a hydrocolloid material comprising gelatin, pectin, sodium carboxymethylcellulose, carboxymethyl cellulose and/or other hygroscopic particles. The flexible material may include a polyurethane film.

Figure 3:
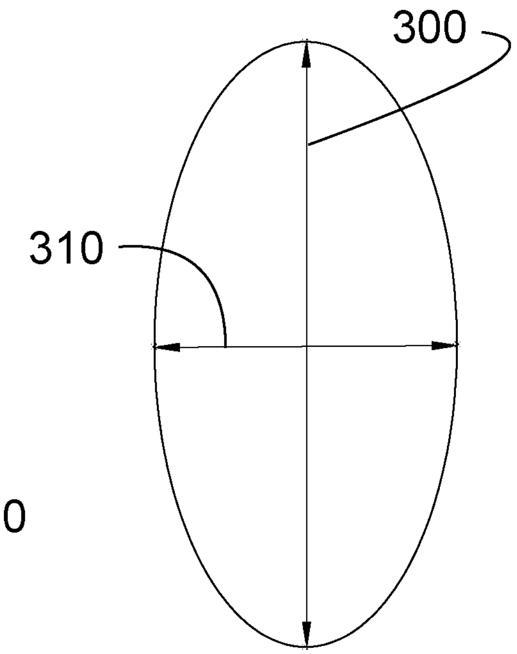
FIG. 3 is a front view of the hydrocolloid heel patch of FIG. 1A showing a major axis and a minor axis.

FIG. 3 is a front view of the hydrocolloid heel patch 100 showing a major axis 300 and a minor axis 310. The patch may be generally ellipse shaped. A common location for a heel fissure, or a dry cracked heel, may be outer edges of the heel. The heel fissure may extend from a side and/or back portion of the heel into a bottom portion of the heel. The ellipse shape may be advantageous for applying the patch 100 proximate a heel fissure. The ellipse shape may facilitate placement of the patch 100 on the side and/or back portion of the heel and the bottom portion of the heel.

The ellipse shape may facilitate application proximate a fissure without modification of the patch 100, i.e., it may be unnecessary to cut a portion of the ellipse and/or modify the ellipse shape in order to apply the patch 100 proximate the fissure. The patch 100 may be configured as a flat ellipse and may be provided to a user in a flat configuration.

The patch 100 may not be configured as a 3-dimensional surface. The patch 100 may be configured as a solid shape and may not include slits, cuts, notches, tabs, and/or other interruptions in the elliptical profile. The patch 100 may not include additional shapes and/or portions extending from the edge of the ellipse.

The patch 100 may include an ellipse shape, wherein the ellipse includes a major axis 300 and a minor axis 310. Additionally, the ellipse may include an aspect ratio defined as the proportion of the length of the major axis to the length of the minor axis. For example, an ellipse with a major axis of 60 mm and a minor axis of 30 mm, will have an aspect ratio of 2:1.

The patch 100 may be configured such that the major axis 300 is within a range less than or equal to 60 mm and the minor axis is within a range less than or equal to 30 mm. In an embodiment, the patch 100 may be one of a set of differently-sized patches, each having a different major axis and/or minor axis.

FIGS. 4A through 4F are a set of differently-sized patches each comprising an ellipse aspect ratio of 2:1. The ellipse aspect ratio of 2:1 may be beneficial in facilitating application of the patch 100 on the side and/or back portion of the heel and the bottom portion of the heel proximate a fissure.

Figure 4A:
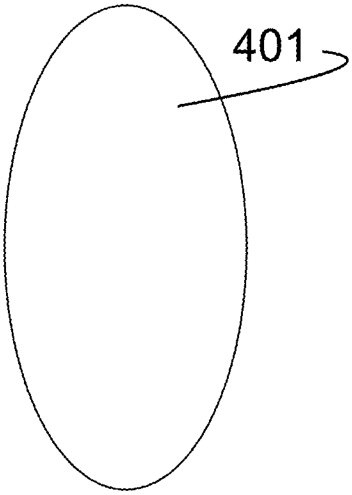
FIG. 4A is a front view of a hydrocolloid heel patch according to an alternate embodiment of the present disclosure.

FIG. 4A is a front view of a hydrocolloid heel patch 401 according to an alternate embodiment of the present disclosure. The patch 401 may include similar features shown and described previously for the patch 100. The patch 401 may include a major axis of approximately 32 mm and a minor axis of approximately 16 mm. The patch 401 may further include an aspect ratio of 2:1.

Figure 4B:
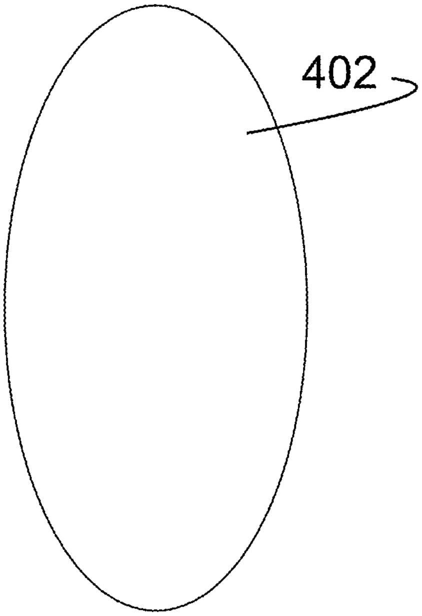
FIG. 4B is a front view of a hydrocolloid heel patch according to an alternate embodiment of the present disclosure.

FIG. 4B is a front view of a hydrocolloid heel patch 402 according to an alternate embodiment of the present disclosure. The patch 402 may include similar features shown and described previously for the patch 100. The patch 402 may include a major axis of approximately 40 mm and a minor axis of approximately 20 mm. The patch 402 may further include an aspect ratio of 2:1.

Figure 4C:
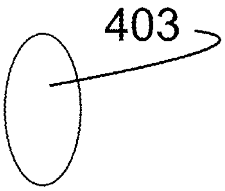
FIG. 4C is a front view of a hydrocolloid heel patch according to an alternate embodiment of the present disclosure.

FIG. 4C is a front view of a hydrocolloid heel patch 403 according to an alternate embodiment of the present disclosure. The patch 403 may include similar features shown and described previously for the patch 100. The patch 403 may include a major axis of approximately 10 mm and a minor axis of approximately 5 mm. The patch 403 may further include an aspect ratio of 2:1.

Figure 4D:
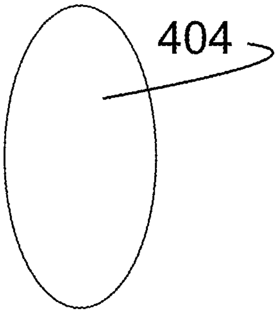
FIG. 4D is a front view of a hydrocolloid heel patch according to an alternate embodiment of the present disclosure.

FIG. 4D is a front view of a hydrocolloid heel patch 404 according to an alternate embodiment of the present disclosure. The patch 404 may include similar features shown and described previously for the patch 100. The patch 404 may include a major axis of approximately 20 mm and a minor axis of approximately 10 mm. The patch 404 may further include an aspect ratio of 2:1.

Figure 4E:
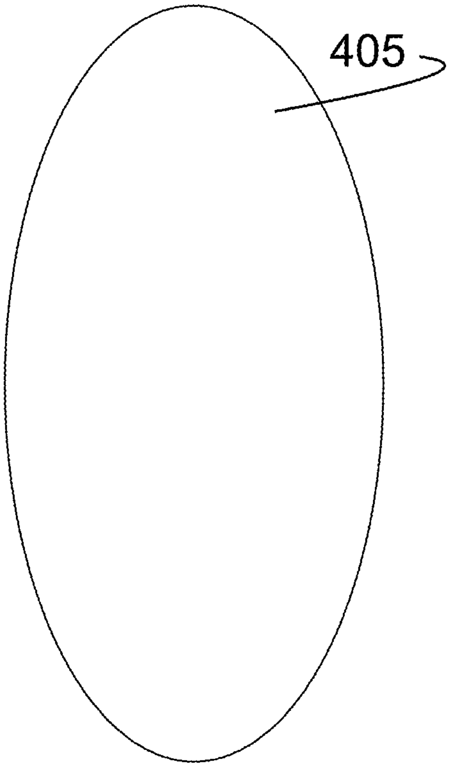
FIG. 4E is a front view of a hydrocolloid heel patch according to an alternate embodiment of the present disclosure.

FIG. 4E is a front view of a hydrocolloid heel patch 405 according to an alternate embodiment of the present disclosure. The patch 405 may include similar features shown and described previously for the patch 100. The patch 405 may include a major axis of approximately 50 mm and a minor axis of approximately 25 mm. The patch 405 may further include an aspect ratio of 2:1.

Figure 4F:
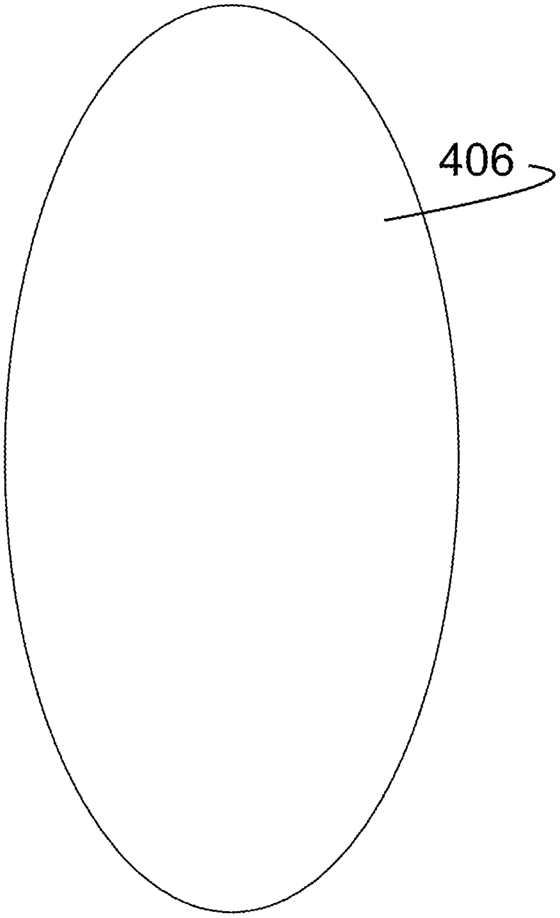
FIG. 4F is a front view of a hydrocolloid heel patch according to an alternate embodiment of the present disclosure.

FIG. 4F is a front view of a hydrocolloid heel patch 406 according to an alternate embodiment of the present disclosure. The patch 406 may include similar features shown and described previously for the patch 100. The patch 406 may include a major axis of approximately 60 mm and a minor axis of approximately 30 mm. The patch 406 may further include an aspect ratio of 2:1.

FIGS. 5A through 5L are a set of differently-sized patches comprising alternate ellipse aspect ratios. Alternate ellipse aspect ratios may be beneficial in facilitating application of the patch 100 on the side and/or back portion of the heel and the bottom portion of the heel proximate a fissure.

Figure 5A:
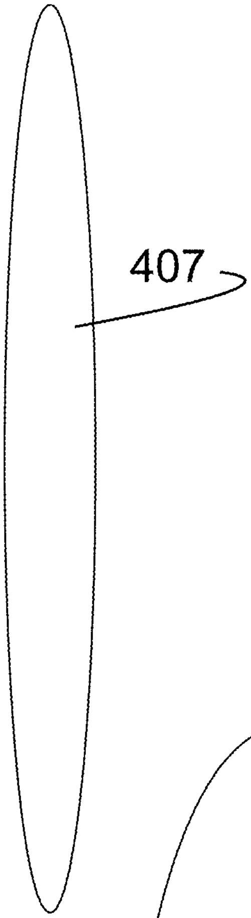
FIG. 5A is a front view of a hydrocolloid heel patch according to an alternate embodiment of the present disclosure.

FIG. 5A is a front view of a hydrocolloid heel patch 407 according to an alternate embodiment of the present disclosure. The patch 407 may include similar features shown and described previously for the patch 100. The patch 407 may include a major axis less than or equal to 60 mm and a minor axis less than or equal to 30 mm. The patch 407 may further include an aspect ratio of 10:1.

Figure 5B:
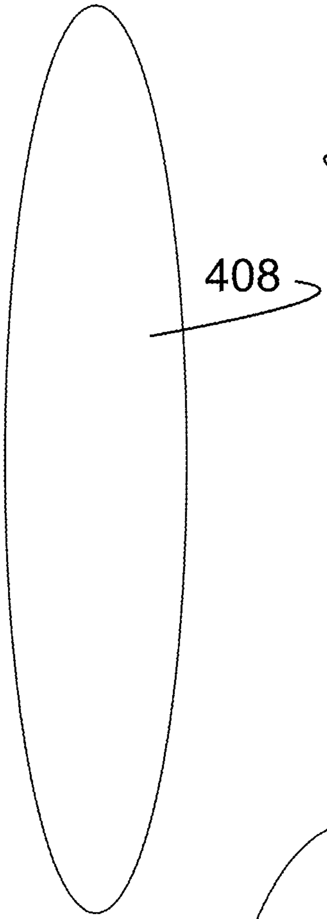
FIG. 5B is a front view of a hydrocolloid heel patch according to an alternate embodiment of the present disclosure.

FIG. 5B is a front view of a hydrocolloid heel patch 408 according to an alternate embodiment of the present disclosure. The patch 408 may include similar features shown and described previously for the patch 100. The patch 408 may include a major axis less than or equal to 60 mm and a minor axis less than or equal to 30 mm. The patch 408 may further include an aspect ratio of 5:1.

Figure 5C:
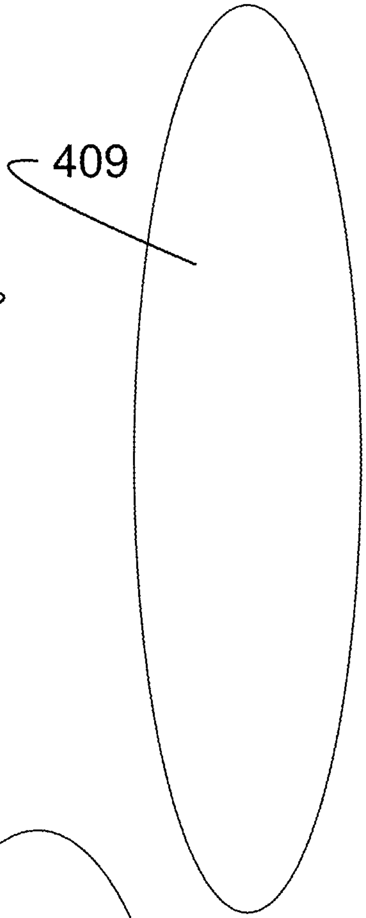
FIG. 5C is a front view of a hydrocolloid heel patch according to an alternate embodiment of the present disclosure.

FIG. 5C is a front view of a hydrocolloid heel patch 409 according to an alternate embodiment of the present disclosure. The patch 409 may include similar features shown and described previously for the patch 100. The patch 409 may include a major axis less than or equal to 60 mm and a minor axis less than or equal to 30 mm. The patch 409 may further include an aspect ratio of 4:1.

Figure 5D:
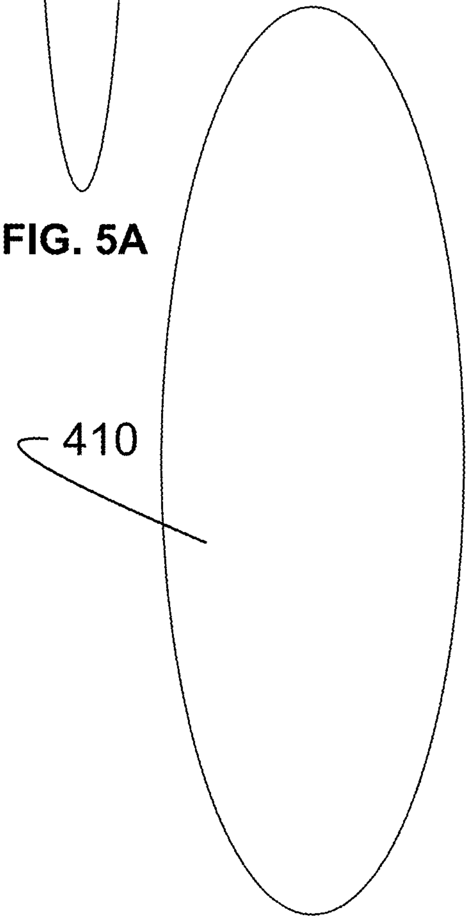
FIG. 5D is a front view of a hydrocolloid heel patch according to an alternate embodiment of the present disclosure.

FIG. 5D is a front view of a hydrocolloid heel patch 410 according to an alternate embodiment of the present disclosure. The patch 410 may include similar features shown and described previously for the patch 100. The patch 410 may include a major axis less than or equal to 60 mm and a minor axis less than or equal to 30 mm. The patch 410 may further include an aspect ratio of 3:1.

Figure 5E:
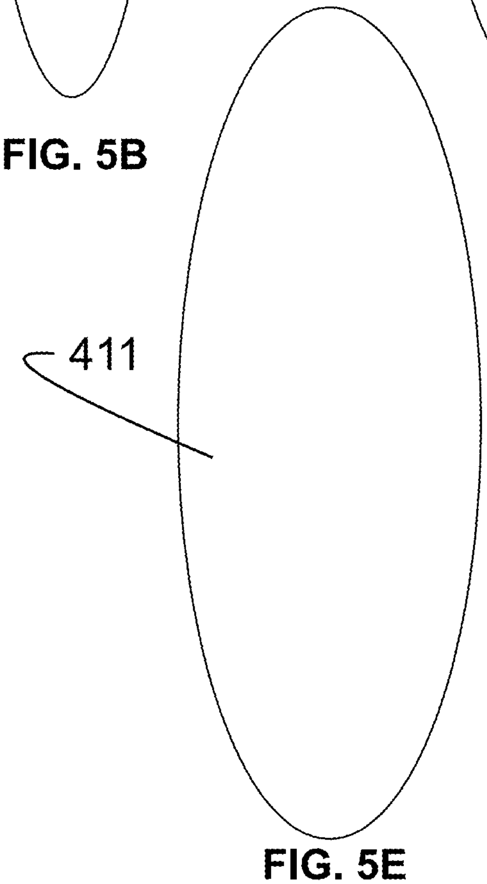
FIG. 5E is a front view of a hydrocolloid heel patch according to an alternate embodiment of the present disclosure.

FIG. 5E is a front view of a hydrocolloid heel patch 411 according to an alternate embodiment of the present disclosure. The patch 411 may include similar features shown and described previously for the patch 100. The patch 411 may include a major axis less than or equal to 60 mm and a minor axis less than or equal to 30 mm. The patch 411 may further include an aspect ratio of 2.75:1.

Figure 5F:
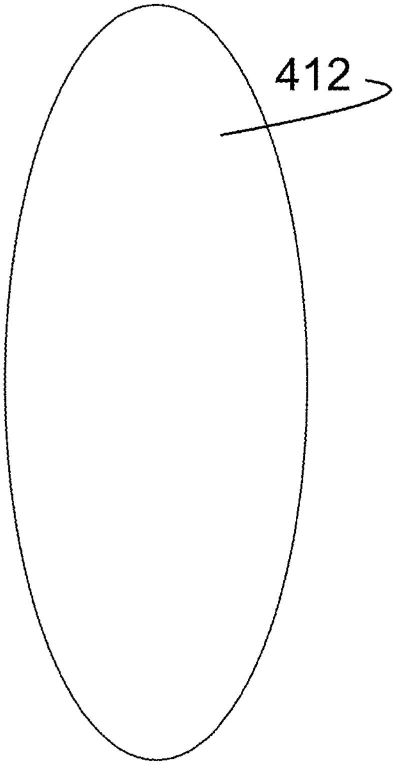
FIG. 5F is a front view of a hydrocolloid heel patch according to an alternate embodiment of the present disclosure

FIG. 5F is a front view of a hydrocolloid heel patch 412 according to an alternate embodiment of the present disclosure. The patch 412 may include similar features shown and described previously for the patch 100. The patch 412 may include a major axis less than or equal to 60 mm and a minor axis less than or equal to 30 mm. The patch 412 may further include an aspect ratio of 2.5:1.

Figure 5G:
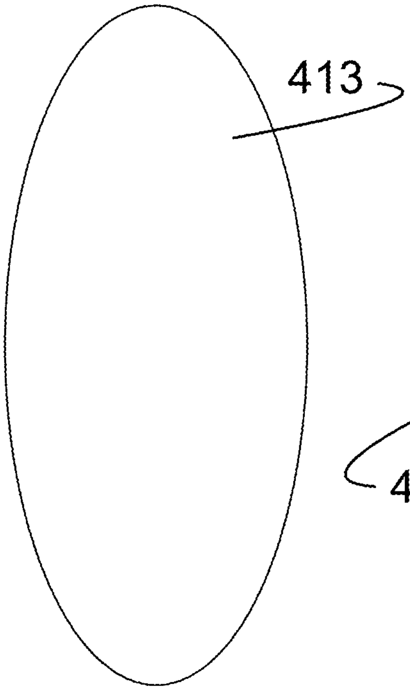
FIG. 5G is a front view of a hydrocolloid heel patch according to an alternate embodiment of the present disclosure

FIG. 5G is a front view of a hydrocolloid heel patch 413 according to an alternate embodiment of the present disclosure. The patch 413 may include similar features shown and described previously for the patch 100. The patch 413 may include a major axis less than or equal to 60 mm and a minor axis less than or equal to 30 mm. The patch 413 may further include an aspect ratio of 2.25:1.

Figure 5H:
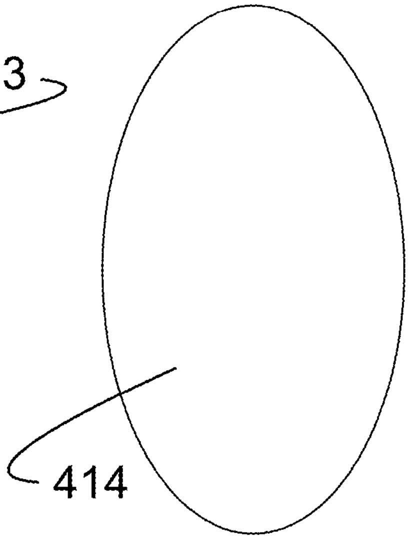
FIG. 5H is a front view of a hydrocolloid heel patch according to an alternate embodiment of the present disclosure

FIG. 5H is a front view of a hydrocolloid heel patch 414 according to an alternate embodiment of the present disclosure. The patch 414 may include similar features shown and described previously for the patch 100. The patch 414 may include a major axis less than or equal to 60 mm and a minor axis less than or equal to 30 mm. The patch 414 may further include an aspect ratio of 1.75:1.

Figure 5J:
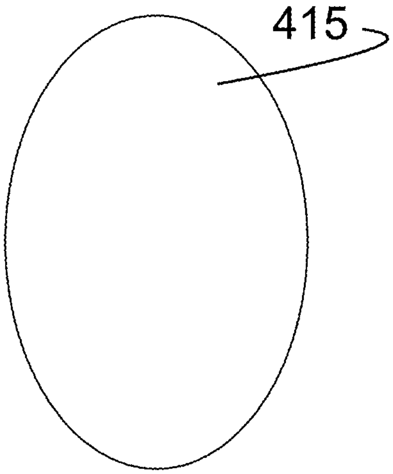
FIG. 5J is a front view of a hydrocolloid heel patch according to an alternate embodiment of the present disclosure

FIG. 5J is a front view of a hydrocolloid heel patch 415 according to an alternate embodiment of the present disclosure. The patch 415 may include similar features shown and described previously for the patch 100. The patch 415 may include a major axis less than or equal to 60 mm and a minor axis less than or equal to 30 mm. The patch 415 may further include an aspect ratio of 1.5:1.

Figure 5K:
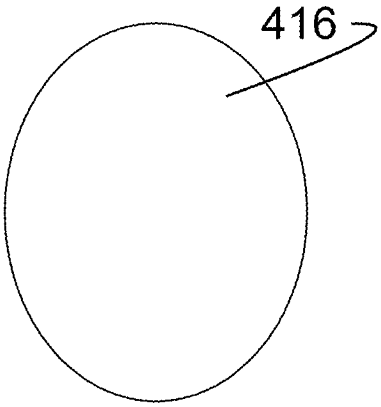
FIG. 5K is a front view of a hydrocolloid heel patch according to an alternate embodiment of the present disclosure

FIG. 5K is a front view of a hydrocolloid heel patch 416 according to an alternate embodiment of the present disclosure. The patch 416 may include similar features shown and described previously for the patch 100. The patch 416 may include a major axis less than or equal to 60 mm and a minor axis less than or equal to 30 mm. The patch 416 may further include an aspect ratio of 1.25:1.

Figure 5L:
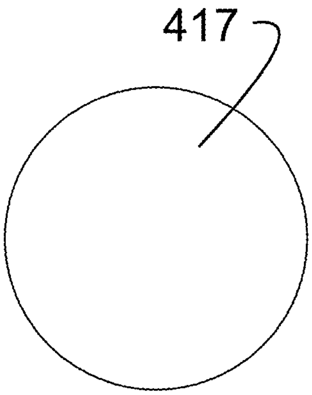
FIG. 5L is a front view of a hydrocolloid heel patch according to an alternate embodiment of the present disclosure.

FIG. 5L is a front view of a hydrocolloid heel patch 417 according to an alternate embodiment of the present disclosure. The patch 417 may include similar features shown and described previously for the patch 100. The patch 417 may include a major axis less than or equal to 60 mm and a minor axis less than or equal to 30 mm. The patch 417 may further include an aspect ratio of 1:1.

Figure 6A:
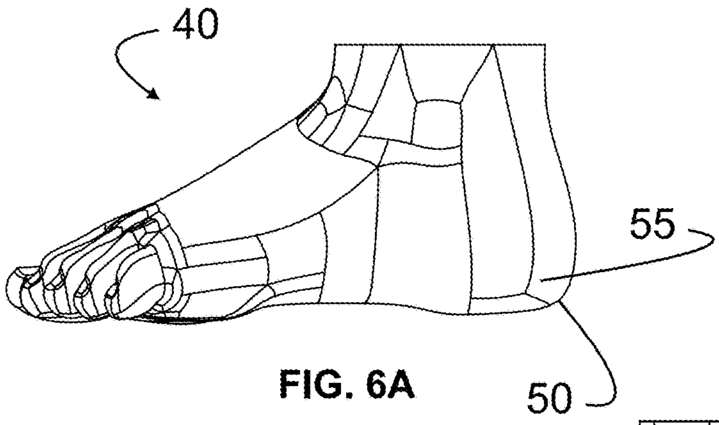
FIG. 6A is a lateral side view of an exemplary foot.
Figure 6B:
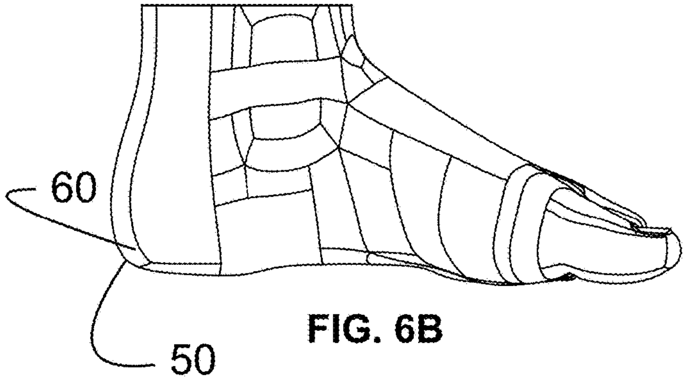
FIG. 6B is a medial side view of an exemplary foot.
Figure 6C:
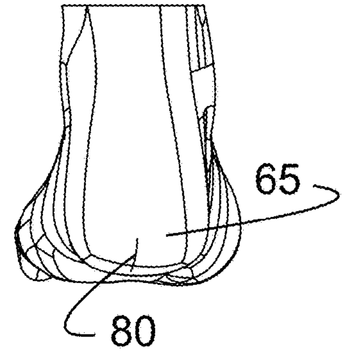
FIG. 6C is a back view of an exemplary foot showing a heel fissure.
Figure 6D:
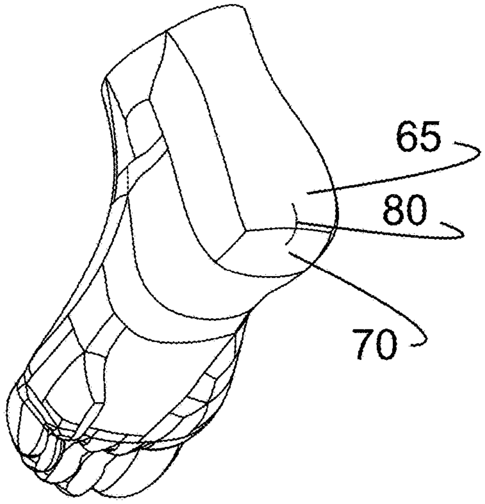
FIG. 6D is a back perspective view of an exemplary foot showing a heel fissure.

FIG. 6A is a lateral side view of an exemplary foot 40, FIG. 6B is a medial side view of an exemplary foot 40, FIG. 6C is a back view of an exemplary foot 40 showing a heel fissure 80, and FIG. 6D is a back perspective view of an exemplary foot 40 showing a heel fissure 80. A common location for a heel fissure 80, or a dry cracked heel, may be outer edges of the heel 50. The heel fissure 80 may extend from a first side 55, a second side 60 and/or back portion 65 of the heel 50 into a bottom portion 70 of the heel 50.

Figure 7A:
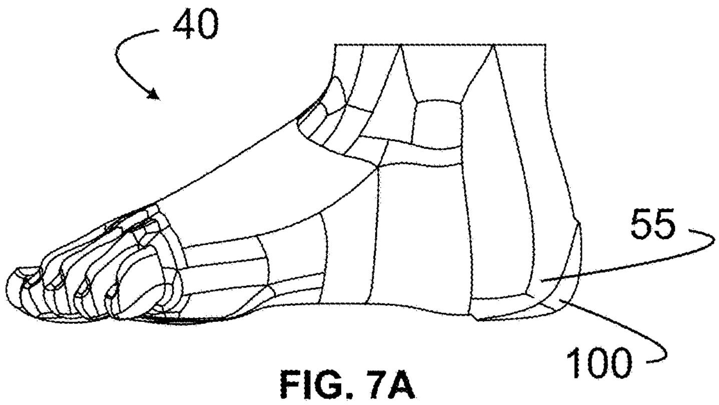
FIG. 7A is a lateral side view of an exemplary foot with a hydrocolloid heel patch according to an embodiment of the present disclosure.
Figure 7B:
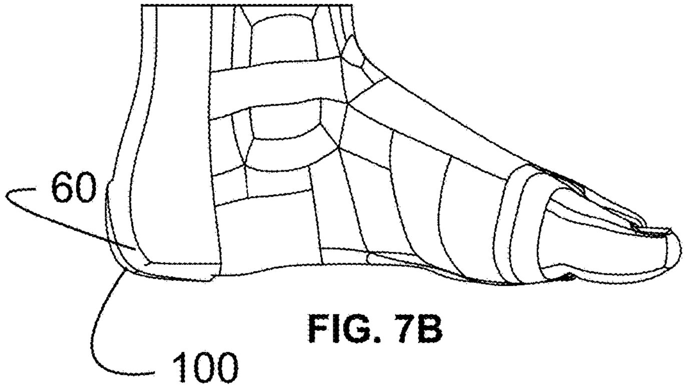
FIG. 7B is a medial side view of an exemplary foot with a hydrocolloid heel patch of FIG. 7A.
Figure 7C:
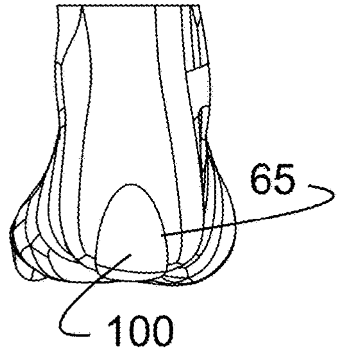
FIG. 7C is a back view of an exemplary foot with a hydrocolloid heel patch of FIG. 7A.
Figure 7D:
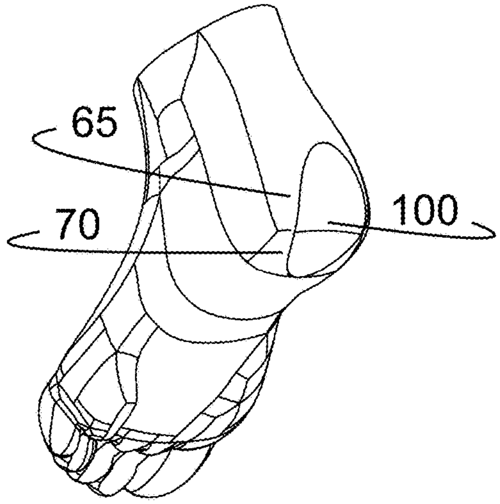
FIG. 7D is a back perspective view of an exemplary foot with a hydrocolloid heel patch of FIG. 7A.

FIG. 7A is a lateral side view of an exemplary foot 40 with a hydrocolloid heel patch 100 according to an embodiment of the present disclosure. FIG. 7B is a medial side view of an exemplary foot 40 with a hydrocolloid heel patch 100, FIG. 7C is a back view of an exemplary foot 40 with a hydrocolloid heel patch 100, and FIG. 7D is a back perspective view of an exemplary foot 40 with a hydrocolloid heel patch 100. The patch 100 may be configured to be applied proximate a heel fissure. The patch 100 may be placed on a side and/or back portion of the heel and the bottom portion of the heel. The patch 100 may be applied proximate a heel fissure without modification to the geometry of the patch 100.

Figure 8:
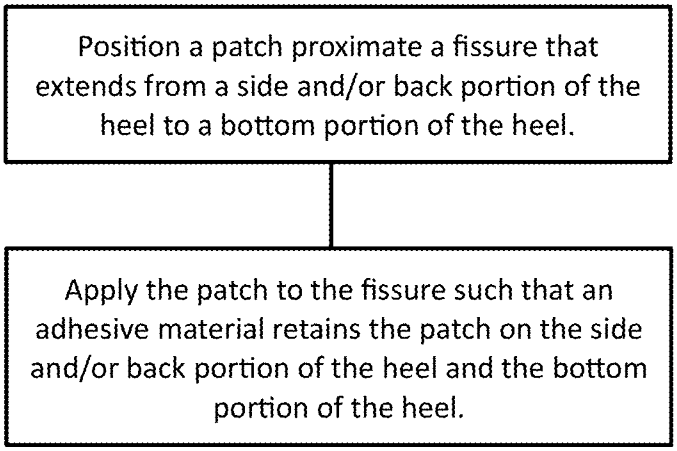
FIG. 8 is a flowchart of a method for treating a fissure of a heel according to an embodiment of the present disclosure.

FIG. 8 is a flowchart of a method for treating a fissure of a heel according to an embodiment of the present disclosure. The method for treating a fissure of a heel may include the following steps:

1. Positioning a patch proximate a fissure that extends from a side and/or back portion of the heel to a bottom portion of the heel.
2. Applying the patch to the fissure such that an adhesive material retains the patch on the side and/or back portion of the heel and the bottom portion of the heel.

Figure 9:
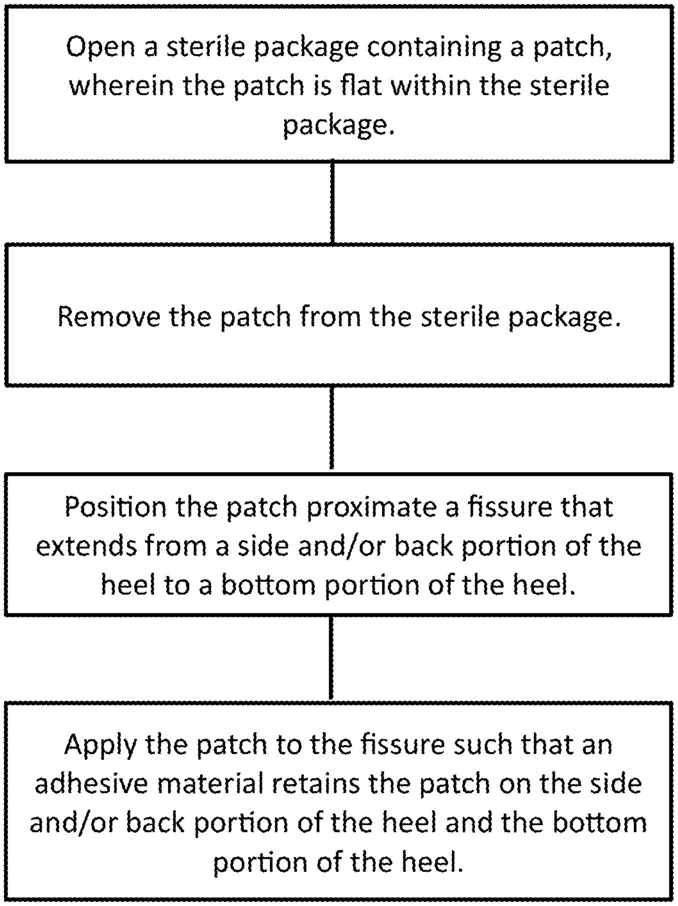
FIG. 9 is a flowchart of a method for treating a fissure of a heel according to an embodiment of the present disclosure.

FIG. 9 is a flowchart of a method for treating a fissure of a heel according to an embodiment of the present disclosure. The method for treating a fissure of a heel may include the following steps:

1. Opening a sterile package containing a patch, wherein the patch is flat within the sterile package.
2. Remove the patch from the sterile package.
3. Positioning the patch proximate a fissure that extends from a side and/or back portion of the heel to a bottom portion of the heel.
4. Applying the patch to the fissure such that an adhesive material retains the patch on the side and/or back portion of the heel and the bottom portion of the heel.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified.

Those of skill in the art will recognize that this is only one of many potential methods that may be used for treating a fissure of a heel. In alternative embodiments, different methods may be used to treat a fissure of a heel using the patch described above. Further, the methods set forth in FIG. 8 and FIG. 9 may be employed to treat a fissure of a heel using other skin treatment patches besides those specifically disclosed herein. Additionally, the methods described above may be used to treat a fissure and/or dry cracked skin on other body parts including an elbow, a ball of a foot, and/or other parts of the body prone to dry cracked skin or fissures.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The phrases "generally parallel" and "generally perpendicular" refer to structures that are within 30° parallelism or perpendicularity relative to each other, respectively. Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the disclosure.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure without departing from its spirit and scope.

What is claimed is:

1. A method for treating a fissure of a heel, wherein the fissure extends from a side and/or back portion of the heel to a bottom portion of the heel, the method comprising:
- positioning a patch proximate the fissure; the patch comprising:
  - an ellipse shape comprising a uniform thickness;
  - an exterior-facing side formed of a flexible material;
  - a skin-facing side comprising an adhesive material configured to adhere only to the skin of the heel;
  - a central portion having a first thickness; and
  - an outer edge having a second thickness equal to the first thickness;
- wherein one of the exterior-facing side and the skin-facing side comprises a hydrocolloid material; and
- applying the patch to the fissure such that the adhesive material retains the patch on the side and/or back portion of the heel and the bottom portion of the heel.

2. The method of claim 1 wherein both the exterior-facing side and the skin-facing side comprise the hydrocolloid material.

3. The method of claim 1, further comprising:
- opening a sterile package containing the patch; and
- removing the patch from the sterile package.

4. The method of claim 1, wherein the ellipse shape comprises an aspect ratio of 2:1.

5. The method of claim 1, wherein the ellipse shape comprises a major axis less than or equal to 60 mm and a minor axis less than or equal to 30 mm.

6. The method of claim 1, wherein the adhesive material is configured so that 1) the patch remains in place after application and 2) the patch is removeable from the heel without causing damage to the skin of the heel or the fissure.

7. A method for treating a fissure of a heel, wherein the fissure extends from a side portion and/or a back portion of the heel to a bottom portion of the heel, the method comprising:
- positioning a patch proximate the fissure; the patch comprising:
  - an exterior-facing side formed of a flexible material; and
  - a skin-facing side comprising an adhesive material configured to adhere to the skin of the heel;
- wherein one of the exterior-facing side and the skin-facing side comprises a hydrocolloid material; and applying the patch to the fissure such that the adhesive material retains the patch only on the bottom portion of the heel and either the side portion or the back portion of the heel;

wherein:

the patch further comprises an ellipse shape comprising a uniform thickness; and the ellipse shape comprises a major axis less than or equal to 60 mm and a minor axis less than or equal to 30 mm.

8. The method of claim 7 wherein both the exterior-facing side and the skin-facing side comprise the hydrocolloid material.

9. The method of claim 8, wherein the ellipse shape comprises an aspect ratio of 2:1.

10. The method of claim 8, wherein the adhesive material is configured so that 1) the patch remains in place after application and 2) the patch is removeable from the heel without causing damage to the skin of the heel or the fissure.

11. The method of claim 7, further comprising:

opening a sterile package containing the patch; and removing the patch from the sterile package.

12. The method of claim 11 wherein the patch is flat within the sterile package.

13. A method for treating a fissure of a heel, wherein the fissure extends from a side and/or back portion of the heel to a bottom portion of the heel, the method comprising:

opening a sterile package containing a patch, wherein the patch is flat within the sterile package, the patch comprising:

an exterior-facing side formed of a flexible material; and a skin-facing side comprising an adhesive material configured to adhere to the skin of the heel;

wherein:

the entire patch comprises a uniform thickness extending between the exterior-facing side and the skin-facing side;

an outer edge of the patch comprises a continuous shape lacking any slits, cuts, notches, or tabs; and one of the exterior-facing side and the skin-facing side comprises a hydrocolloid material;

removing the patch from the sterile package;

positioning the patch proximate the fissure; and applying the patch to the fissure such that the adhesive material retains the patch on the side and/or back portion of the heel and the bottom portion of the heel.

14. The method of claim 13 wherein both the exterior-facing side and the skin-facing side comprise the hydrocolloid material.

15. The method of claim 13, wherein the patch further comprises an ellipse shape comprising the uniform thickness.

16. The method of claim 15, wherein the ellipse shape comprises an aspect ratio of 2:1.

17. The method of claim 15, wherein the ellipse shape comprises a major axis less than or equal to 60 mm and a minor axis less than or equal to 30 mm.

18. The method of claim 13, wherein the adhesive material is configured so that 1) the patch remains in place after application and 2) the patch is removeable from the heel without causing damage to the skin of the heel or the fissure.

19. The method of claim 13, wherein the adhesive material is configured to adhere only to the skin of the heel.

* * * * *